US00PP16131P3

(12) United States Plant Patent
Lim

(10) Patent No.: US PP16,131 P3
(45) Date of Patent: Nov. 29, 2005

(54) SHRUB ROSE PLANT NAMED 'BAIFAIRY'

(50) Latin Name: *Rosa hybrida*
Varietal Denomination: BAIfairy

(75) Inventor: Peter P. Lim, Yamhill, OR (US)

(73) Assignee: Bailey Nurseries, Inc., St. Paul, MN (US)

( * ) Notice: Subject to any disclaimer, the term of this patent is extended or adjusted under 35 U.S.C. 154(b) by 66 days.

(21) Appl. No.: 10/769,746

(22) Filed: Feb. 3, 2004

(65) Prior Publication Data

US 2005/0172371 P1 Aug. 4, 2005

(51) Int. Cl.[7] ..... A01H 5/00
(52) U.S. Cl. ..... Plt./108

(58) Field of Search ..... Plt./102, 107, 108, Plt./130, 101, 138, 139, 140

*Primary Examiner*—Howard J. Locker
(74) *Attorney, Agent, or Firm*—Burns, Doane, Swecker & Mathis, LLP

(57) ABSTRACT

A new and distinct variety of shrub rose plant is provided which abundantly forms on a continuous basis double rich red blossoms blended with pink that fade to deep pink at full maturity. The blossoms also display a slight sweet rose fragrance. The plant exhibits a compact and bushy growth habit, satiny medium green foliage that initially bears a tint of red-purple, and good tolerance to Black Spot and Powdery Mildew. The attractive medium green foliage contrasts nicely with the blossom coloration. The new variety is particularly well suited for growing as attractive ornamentation in parks and gardens.

1 Drawing Sheet

Botanical commercial classification: *Rosa hybrida*/Shrub Rose Plant.
Varietal denomination: cv. 'BAIfairy'.

SUMMARY OF THE INVENTION

The new variety of *Rosa hybrida* shrub rose plant was created at Yamhill, Oreg. during 1995 by artificial pollination wherein two parents were crossed which previously had been studied in the hope that they would contribute the desired characteristics. The female parent (i.e., the seed parent) was the *Rosa polyantha* 'The Fairy' variety (non-patented in the United States). The male parent (i.e., the pollen parent) was the 'MEIgekanu' variety (U.S. Plant Pat. No. 6,384). The 'MEIgekanu' variety sometimes is marketed under the LA SEVILLANA trademark. The parentage of the new variety can be summarized as follows:

'The Fairy'×'MEIgekanu'.

The seeds resulting from the above pollination were sown and plants were obtained which were physically and biologically different from each other. Selective study resulted in the identification during 1998 of a single plant of the new variety having the distinctive ornamental characteristics hereafter described.

It was found that the new variety of the present invention:

(a) exhibits a compact and bushy growth habit, (b) abundantly forms on a continuous basis in clusters attractive double rich red blossoms blended with pink that fade to deep pink at full maturity, (c) forms satiny medium green foliage that initially bears a tint of red-purple, (d) displays good tolerance to Black Spot and Powdery Mildew; and (e) is particularly well suited for growing as attractive ornamentation in parks and gardens.

The young red flower buds open to red blooms blended with pink that fade to deep pink. The aging petals commonly detach cleanly and do not detract from the attractiveness of the blooms. Good hardiness is also displayed by the new variety.

The new variety well meets the needs of the horticultural industry and can be grown to advantage in the landscape where attractive ornamentation is desired. The distinctive blossoms are displayed throughout the season. The plant can be grown as a specimen or as a mass planting.

The new variety can be readily distinguished from other varieties including its ancestors. For instance, the blossoms of 'The Fairy' variety are pink and the blossoms of the 'MEIgekanu' variety are vermilion in coloration.

The new variety has been found to undergo asexual propagation by budding on an understock and by the rooting of cuttings. 'Dr. Huey' rootstock was used during the budding. Such asexual propagation by these techniques at Yamhill, Oreg., St. Paul, Minn., and at Phoenix, Ariz. has shown that the characteristics of the new variety are stable and are strictly transmissible by such asexual propagation from one generation to another. The new variety grows well on its own roots.

Initially the new plant was designated 95M574-IR. The new variety subsequently has been named the 'BAIfairy' variety, and currently is being marketed while using the MYSTIC FAIRY and GARDEN PATH trademarks.

BRIEF DESCRIPTION OF THE PHOTOGRAPHS

The accompanying photographs show as nearly true as it is reasonably possible to make the same in a color illustrations of this character, typical specimens of the new variety. The rose plants of the new variety had been propagated by the rooting of cuttings, were approximately two years of age, and were being grown outdoors St. Paul, Minn.

DETAILED DESCRIPTION

The chart used in the identification of the colors is that of The Royal Horticultural Society (R.H.S. Colour Chart). Common color terms are to be accorded their ordinary dictionary significance. The description is based on the observation of three and four year-old plants while grown outdoors on their own roots during June 2002 at Yamhill, Oreg., and July 2003 at St. Paul, Minn.

Botanical classification: *Rosa hybrida*, var. 'BAIfairy'.
Class: Shrub.
Plant:
- *Height.*—Approximately 90 cm on average at the end of the growing season.
- *Width.*—Approximately 100 cm on average at the end of the growing season.
- *Habit.*—Compact, rounded to substantially square, and bushy.

Branches:
- *Color.*—Young stems: commonly between Greyed-Purple Group 184A and 185B. Adult wood: Green Group 137C with highlights of Greyed-Purple Group 184B.
- *Thorns.*—Size: commonly approximately 0.15 to 0.50 cm in length. Color: commonly between Greyed-Purple Group 187A and 187B.

Leaves:
- *Stipules.*—Generally parallel with the auricle facing outward.
- *Petioles.*—Upper surface: Yellow-Green Group 148C with highlights of Greyed-Purple Group 184B and 184C. Under surface: Yellow-Green Group 148C with highlights of Greyed-Purple Group 184C.
- *Leaflets.*—Number: 3, 5 (most often), and 7. Shape: ovate with a rounded base and an acuminate tip. Serration: serrulate. Texture: bears a satiny finish. General appearance: medium green with a satiny surface when mature. Color (young foliage): Upper surface: Green Group 138A with highlights of Greyed-Purple Group 185A and 185B. Under surface: Greyed-Purple Group 185B with highlights of Green Group 138A. Color (adult foliage): Upper surface: Green Group 137B with some Greyed-Purple Group 187B at the margin. Under surface: commonly between Green Group 138A and 138B.

Figure 1:
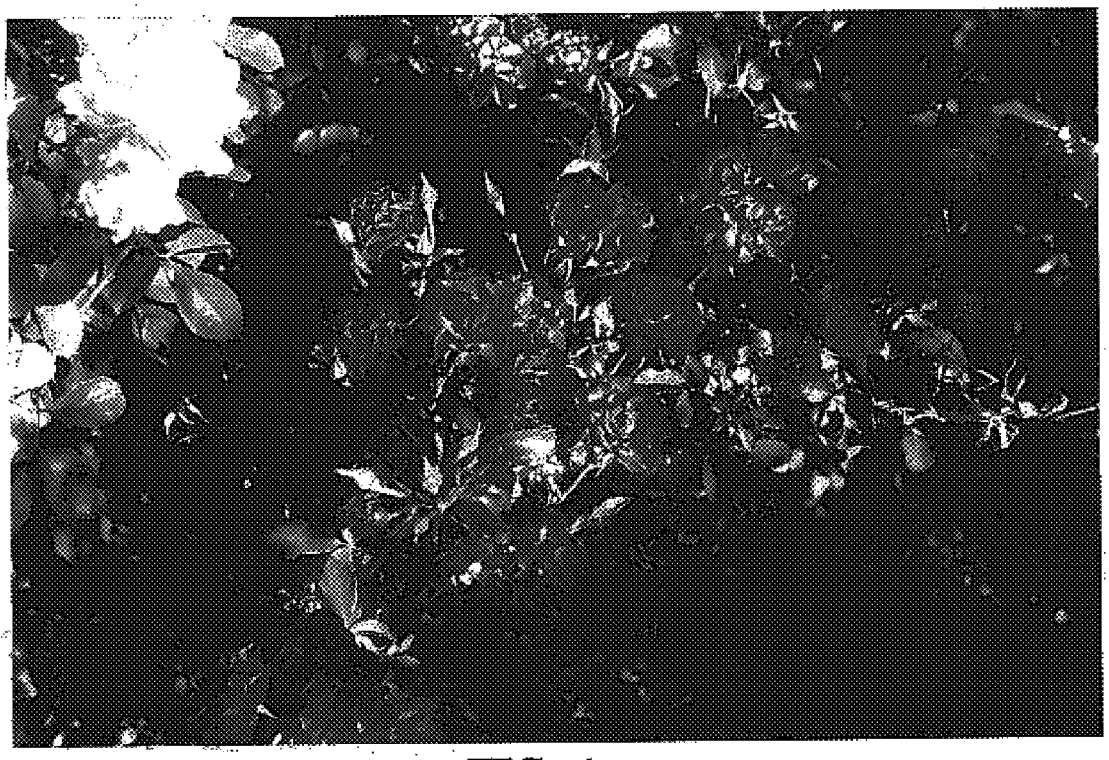
FIG. 1 illustrates typical blossoms in various stages of opening and foliage of the new variety. Clusters of attractive double rich red blossoms blended with pink are shown.
Figure 2:
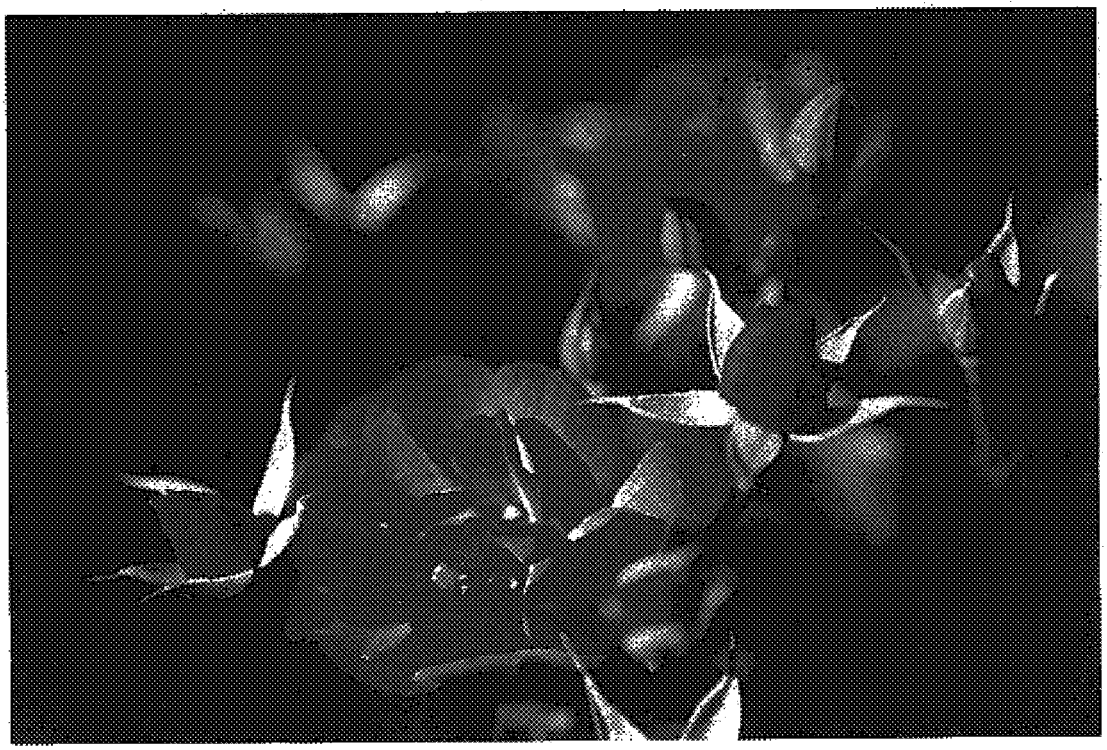
FIG. 2 illustrates a close view of buds and a typical flower of the new variety. The sepals also are shown in detail.

Inflorescence:
- *Number of flowers.*—Commonly approximately 10 blooms on average per cluster.
- *Peduncle.*—With some prickles, near Yellow-Green Group 144B in coloration, and the length is approximately 3 cm on average.
- *Sepals.*—Upper surface: commonly between Green Group 141B and 141C in coloration. Under surface: near Green Group 141A with areas of White Group 155D, and some pubescence. Size: approximately 2.25 cm in length with some minute extensions as shown in FIG. 2.
- *Buds.*—Shape: generally rounded. Size: small. Length: approximately 1.5 cm on average. Diameter: approximately 1.0 cm on average. Color: Upper surface: Red Group 53B blending to Red Group 52A at the base. Under surface: Red Group 53A blending to Red Group 53C at the base.
- *Flower.*—Shape: double and somewhat informal. Diameter: approximately 5 cm on average. Color (when opening begins): Upper surface: Red Group 53C. Under surface: Red Group 53B and 53C. Color (when blooming): Upper surface: between Red Group 51A and 53D. Under surface: Red Group 54A with highlights of Red Group 53C. Color (at end of blooming): Upper surface: Red Group 51A with highlights of Red Group 54C. Under surface: Red Group 52A with highlights of Red Group 54B. Color (basal petal spot): Yellow Group 3D. Fragrance: slight sweet rose. Lasting quality: the blossoms commonly last approximately 4 to 6 days on average depending upon the temperature and sunlight exposure. Petal number: approximately 27 on average under normal growing conditions. Petal shape: wedge-shaped commonly with a curled apex when fully open. Petal drop: commonly the petals detach cleanly at full blossom maturity. Anthers: near Yellow Group 7A in coloration. Filament number: commonly approximately 56 on average. Filament color: near Yellow-Green Group 151B in coloration. Pistils: approximately 35 on average. Stigmas: near Yellow-Green Group 151C in coloration. Styles: commonly between Yellow-Green Group 145B and 145C in coloration. Hips: none observed. Receptacle: separate and free with achenes at the bottom and center.

Development:
- *Vegetation.*—Vigorous, and compact.
- *Blooming.*—Abundant on strong canes and continuous throughout the season.
- *Resistance to diseases.*—Highly tolerant to Black Spot, and Powdery Mildew.
- *Hardiness zone.*—U.S.D.A. Hardiness Zone Nos. 4 to 7.

I claim:

1. A new and distinct variety of shrub rose plant characterized by the following combination of characteristics:
(a) exhibits a compact and bushy growth habit,
(b) abundantly forms on a continuous basis in clusters attractive double rich red blossoms blended with pink that fade to deep pink at full maturity,
(c) forms satiny medium green foliage that initially bears a tint of red-purple,
(d) displays good tolerance to Black Spot and Powdery Mildew, and
(e) is particularly well suited for growing as attractive ornamentation in parks and gardens;
substantially as herein shown and described.

* * * * *